(12) United States Patent
Ebata

(10) Patent No.: US 12,036,070 B2
(45) Date of Patent: *Jul. 16, 2024

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,093

(22) Filed: Mar. 22, 2023

(65) Prior Publication Data

US 2023/0225705 A1 Jul. 20, 2023

Related U.S. Application Data

(63) Continuation of application No. 16/354,546, filed on Mar. 15, 2019, now Pat. No. 11,642,101, which is a
(Continued)

(30) Foreign Application Priority Data

Sep. 26, 2016 (JP) ................. 2016-187003

(51) Int. Cl.
*A61B 8/00* (2006.01)
*A61B 8/08* (2006.01)
*A61B 8/14* (2006.01)

(52) U.S. Cl.
CPC .............. *A61B 8/4254* (2013.01); *A61B 8/14* (2013.01); *A61B 8/4245* (2013.01); *A61B 8/461* (2013.01);
(Continued)

(58) Field of Classification Search
None
See application file for complete search history.

(56) References Cited

U.S. PATENT DOCUMENTS 6,607,488 B1 8/2003 Jackson et al.
2007/0055153 A1 3/2007 Simopoulos et al.
(Continued)

FOREIGN PATENT DOCUMENTS

CN 101002681 A 7/2007
CN 104968280 A 10/2015
(Continued)

OTHER PUBLICATIONS

Advisory Action issued in U.S. Appl. No. 16/354,546 on Oct. 20, 2021.
(Continued)

*Primary Examiner* — Katherine L Fernandez
(74) *Attorney, Agent, or Firm* — Birch, Stewart, Kolasch & Birch, LLP

(57) ABSTRACT

Provided is an ultrasound diagnostic apparatus including an ultrasound probe, an imaging section that images the subject on the basis of a reception signal output from the ultrasound probe to generate an ultrasound image, an image analysis section that performs image analysis using the ultrasound image, a movement detection sensor that detects and outputs a movement of the ultrasound probe as a detection signal, a movement amount calculation section that calculates a movement amount of the ultrasound probe in a case where an imaging inspection portion that is currently being imaged among a plurality of inspection portions of the subject is inspected, using the detection signal output from the movement detection sensor, and a portion discrimination section that discriminates the imaging inspection portion on the basis of an image analysis result in the image analysis
(Continued)

section and the movement amount calculated by the movement amount calculation section.

9 Claims, 6 Drawing Sheets

Related U.S. Application Data continuation of application No. PCT/JP2017/015464, filed on Apr. 17, 2017.

(52) U.S. Cl.
CPC .......... *A61B 8/5207* (2013.01); *A61B 8/5223* (2013.01); *A61B 8/5276* (2013.01); *A61B 8/54* (2013.01)

(56) References Cited

U.S. PATENT DOCUMENTS

| | | | | |
|---|---|---|---|---|
| 2008/0154123 | A1* | 6/2008 | Jackson | A61B 8/4254 |
| | | | | 600/424 |
| 2011/0125018 | A1 | 5/2011 | Shin et al. | |
| 2012/0203106 | A1* | 8/2012 | Matsunaga | A61B 8/06 |
| | | | | 600/443 |
| 2015/0245823 | A1 | 9/2015 | Jin et al. | |
| 2015/0374343 | A1 | 12/2015 | Shan et al. | |
| 2016/0135789 | A1 | 5/2016 | Takeuchi et al. | |
| 2018/0129782 | A1* | 5/2018 | Himsl | G16H 30/20 |
| 2019/0192121 | A1 | 6/2019 | Ebata | |

FOREIGN PATENT DOCUMENTS

| | | |
|---|---|---|
| JP | 4-224738 A | 8/1992 |
| JP | 2007-167118 A | 7/2007 |
| JP | 2010-63647 A | 3/2010 |
| JP | 2010-253031 A | 11/2010 |
| JP | 2010-259662 A | 11/2010 |
| JP | 2011-110431 A | 6/2011 |
| JP | 2013-111309 A | 6/2013 |
| JP | 2016-96881 A | 5/2016 |

OTHER PUBLICATIONS

Chinese Office Action and Search Report for corresponding Chinese Application No. 201780058638.2 dated Mar. 8, 2021, with an English translation.
Chinese Office Action for corresponding Chinese Application No. 201780058638.2, dated Dec. 20, 2021, with an English translation.
Extended European Search Report for corresponding European Application No. 17852602.6, dated Sep. 19, 2019.
Final Office Action issued in U.S. Appl. No. 16/354,546 on Jul. 21, 2021.
Final Office Action issued in U.S. Appl. No. 16/354,546 on Sep. 19, 2022.
International Preliminary Report on Patentability and Written Opinion of the International Searching Authority(Forms PCT/IB/326, PCT/IB/373 and PCT/ISA/237), dated Apr. 4, 2019, for International Application No. PCT/JP2017/015464, with an English Translation of the Written Opinion.
International Search Report (Form PCT/ISA/210), dated Jun. 27, 2017, for International Application No. PCT/JP2017/015464, with an English translation.
Non-Final Office Action issued in U.S. Appl. No. 16/354,546 on Feb. 16, 2022.
Non-Final Office Action issued in U.S. Appl. No. 16/354,546 on Feb. 24, 2021.
Notice of Allowance issued in U.S. Application No. 16/354,546 on Dec. 22, 2022.
Office Action issued Sep. 8, 2021 in corresponding Chinese Patent Application No. 201780058638.2, with English translation.
Restriction Requirement issued in U.S. Appl. No. 16/354,546 on Dec. 8, 2020.

\* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of U.S. patent application Ser. No. 16/354,546, filed Mar. 15, 2019, which is a Continuation of PCT International Application No. PCT/JP2017/015464 filed on Apr. 17, 2017, which claims priority under 35 U.S.C. § 119(a) to Japanese Patent Application No. 2016-187003 filed on Sep. 26, 2016. The above applications are hereby expressly incorporated by reference, in their entirety, into the present application.

BACKGROUND OF THE INVENTION

1. Field of the Invention

The present invention relates to an ultrasound diagnostic apparatus and a control method of the ultrasound diagnostic apparatus, and more particularly, to an ultrasound diagnostic apparatus that discriminates an inspection portion that is currently being imaged.

2. Description of the Related Art

In the related art, an ultrasound diagnostic apparatus that uses an ultrasound image has been put to practical use in a medical field. Generally, such an ultrasound diagnostic apparatus operates an ultrasound beam into a subject from an ultrasound probe in which an array transducer is provided, receives an ultrasound echo from the subject using the ultrasound probe to output a reception signal, and electrically processes the reception signal to generate an ultrasound image.

In a case where a plurality of inspection portions of the subject are diagnosed using such an ultrasound image, in order to obtain ultrasound images suitable for diagnosis with respect to the respective inspection portions, it is necessary to set different appropriate imaging conditions in accordance with the inspection portions. In this regard, for example, JP-H4-224738A (JP1992-224738A) discloses an ultrasound diagnostic apparatus that automatically discriminates an inspection portion from a generated ultrasound image through a pattern matching process and sets imaging conditions suitable for the inspection portion on the basis of the discrimination result.

SUMMARY OF THE INVENTION

However, since an ultrasound image is changed due to various causes such as a difference between shapes of inspection portions and a difference between dynamic ranges or brightnesses due to a difference between passage easinesses of ultrasound for the inspection portions, there is a concern that the inspection portions may be mistakenly discriminated only using the discrimination of the inspection portions based on the ultrasound image. In this case, there is a concern that inappropriate imaging conditions may be set on the basis of the mistaken discrimination result and an ultrasound image with a low image quality may be generated to cause an error in diagnosis.

The invention has been made in consideration of the problems in the related art, and an object of the invention is to provide an ultrasound diagnostic apparatus and a control method of the ultrasound diagnostic apparatus capable of accurately discriminating an inspection portion.

According to an aspect of the invention, there is provided an ultrasound diagnostic apparatus comprising: an ultrasound probe; an imaging section that performs transmission and reception of an ultrasound beam between a subject and the ultrasound probe and images the subject on the basis of a reception signal output from the ultrasound probe to generate an ultrasound image; an image analysis section that performs image analysis using the ultrasound image generated by the imaging section; a movement detection sensor that is attached to the ultrasound probe and detects a movement of the ultrasound probe to output the movement as a detection signal; a movement amount calculation section that calculates a movement amount of the ultrasound probe in a case where an imaging inspection portion that is currently being imaged among a plurality of inspection portions of the subject is inspected, using the detection signal output from the movement detection sensor; and a portion discrimination section that discriminates the imaging inspection portion on the basis of an image analysis result in the image analysis section and the movement amount calculated by the movement amount calculation section.

The portion discrimination section may integrate the image analysis result in the image analysis section and the movement amount calculated by the movement amount calculation section to discriminate the imaging inspection portion.

Further, it is preferable that the image analysis section performs the image analysis using the ultrasound image to calculate a feature amount of the ultrasound image, and the portion discrimination section integrates the feature amount calculated by the image analysis section and the movement amount calculated by the movement amount calculation section to discriminate the imaging inspection portion.

Further, the portion discrimination section may narrow down the plurality of inspection portions that are targets of the image analysis, on the basis of the movement amount calculated by the movement amount calculation section, the image analysis section may perform the image analysis with respect to the inspection portions narrowed down by the portion discrimination section, and the portion discrimination section may discriminate the imaging inspection portion using the image analysis result in the image analysis section.

Alternatively, the portion discrimination section may determine an analysis order for performing the image analysis with respect to the plurality of inspection portions, on the basis of the movement amount calculated by the movement amount calculation section, the image analysis section may sequentially perform the image analysis with respect to the plurality of inspection portions in accordance with the analysis order determined by the portion discrimination section, and the portion discrimination section may discriminate the imaging inspection portion using the image analysis result in the image analysis section.

It is preferable that the ultrasound diagnostic apparatus further comprises: a movement amount reference value memory in which a plurality of movement amount reference values corresponding to the plurality of inspection portions of the subject and relating to the movement amount are stored in advance. Further, it is preferable that the portion discrimination section reads out the plurality of movement amount reference values from the movement amount reference value memory, compares each of the plurality of read-out movement amount reference values with the movement amount calculated by the movement amount calculation section, and discriminates the imaging inspection portion on the basis of the comparison result and the image analysis result in the image analysis section.

It is preferable that the ultrasound diagnostic apparatus further comprises: a probe operating information memory in which information relating to an operation of the ultrasound probe is stored in advance for each inspector or each subject. Further, it is preferable that the portion discrimination section reads out the information relating to the operation of the ultrasound probe from the probe operating information memory, corrects the plurality of movement amount reference values on the basis of the read-out information, compares each of the plurality of corrected movement amount reference values with the movement amount calculated by the movement amount calculation section, and discriminates the imaging inspection portion on the basis of the comparison result and the image analysis result in the image analysis section.

The ultrasound diagnostic apparatus may further comprise: an imaging condition setting section that sets an imaging condition corresponding to the imaging inspection portion discriminated by the portion discrimination section, and the imaging section may generate the ultrasound image in accordance with the imaging condition set by the imaging condition setting section.

It is preferable that the movement detection sensor is formed by an acceleration sensor, a gyro sensor, a magnetic sensor, or a GPS sensor.

According to another aspect of the invention, there is provided a control method of an ultrasound diagnostic apparatus comprising: performing transmission and reception of an ultrasound beam between a subject and an ultrasound probe and imaging the subject on the basis of a reception signal output from the ultrasound probe to generate an ultrasound image; performing image analysis using the generated ultrasound image; detecting a movement of the ultrasound probe to output the movement as a detection signal; calculating a movement amount of the ultrasound probe in a case where an imaging inspection portion that is currently being imaged among a plurality of inspection portions of the subject is inspected, using the output detection signal; and discriminating the imaging inspection portion on the basis of an image analysis result and the calculated movement amount.

According to the invention, since the ultrasound diagnostic apparatus comprises an ultrasound probe; an imaging section that performs transmission and reception of an ultrasound beam between a subject and the ultrasound probe and images the subject on the basis of a reception signal output from the ultrasound probe to generate an ultrasound image; an image analysis section that performs image analysis using the ultrasound image generated by the imaging section; a movement detection sensor that is attached to the ultrasound probe and detects a movement of the ultrasound probe to output the movement as a detection signal; a movement amount calculation section that calculates a movement amount of the ultrasound probe in a case where an imaging inspection portion that is currently being imaged among a plurality of inspection portions of the subject is inspected, using the detection signal output from the movement detection sensor; and a portion discrimination section that discriminates the imaging inspection portion on the basis of an image analysis result in the image analysis section and the movement amount calculated by the movement amount calculation section, it is possible to accurately discriminate an inspection portion.

DESCRIPTION OF THE PREFERRED EMBODIMENTS

Hereinafter, embodiments of the invention will be described on the basis of the accompanying drawings.

Embodiment 1

Figure 1:
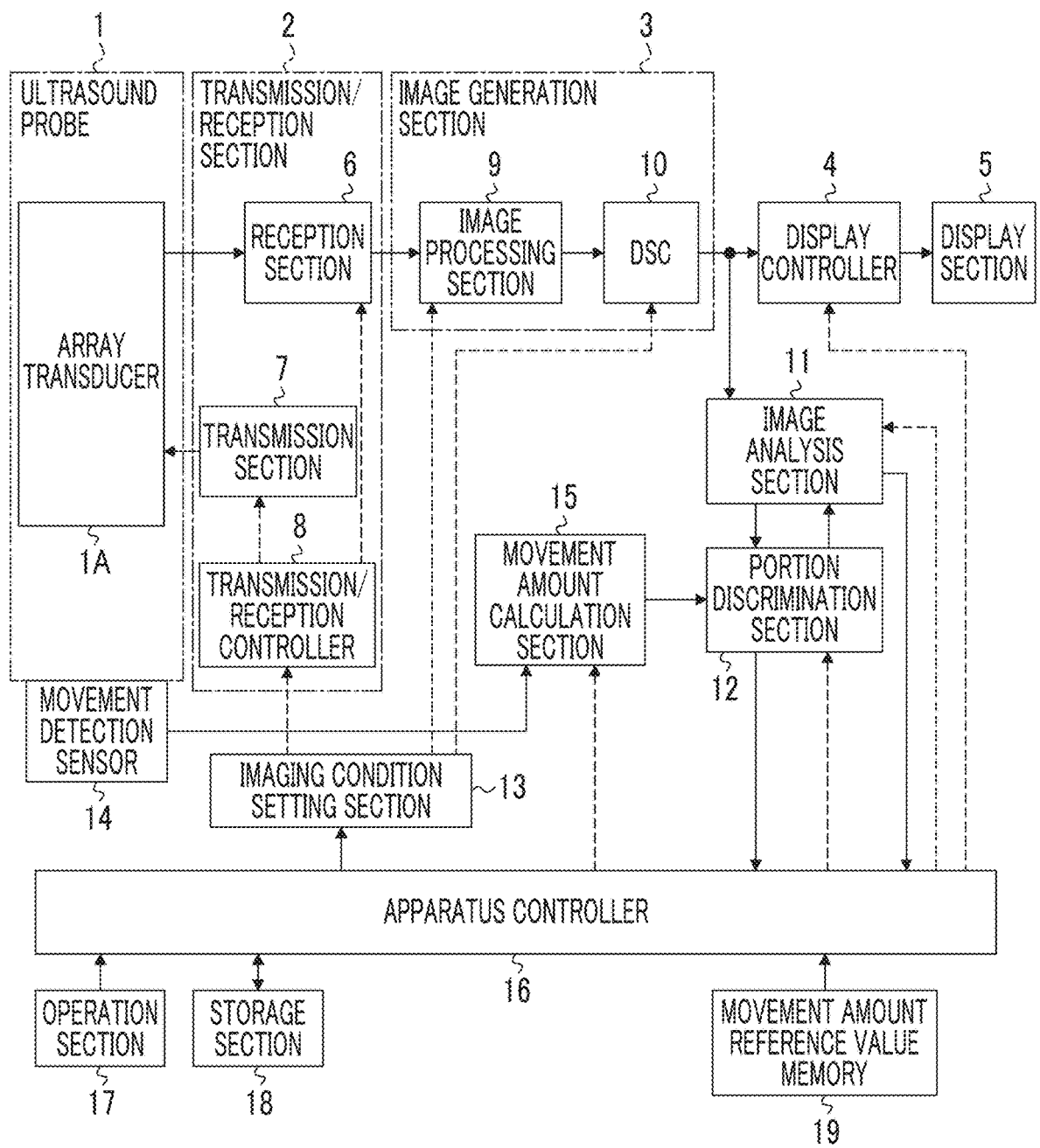
FIG. 1 is a diagram showing a configuration of ultrasound diagnostic apparatus according to Embodiment 1 of the invention.

FIG. 1 shows a configuration of an ultrasound diagnostic apparatus according to Embodiment 1. The ultrasound diagnostic apparatus comprises an ultrasound probe 1 in which an array transducer 1A is provided, an image generation section 3 that is connected to the ultrasound probe 1 through a transmission/reception section 2, and a display section 5 that is connected to the image generation section 3 through a display controller 4.

The transmission/reception section 2 includes a reception section 6 and a transmission section 7 that are connected to the array transducer 1A, and a transmission/reception controller 8 that is connected to the reception section 6 and the transmission section 7. The image generation section 3 includes an image processing section 9 and a digital scan converter (DSC) 10 that is connected to the image processing section 9. The display controller 4 is connected to the DSC 10. Further, an image analysis section 11 is connected to the DSC 10, and a portion discrimination section 12 is connected to the image analysis section 11.

An imaging condition setting section 13 is connected to the transmission/reception controller 8 of the transmission/reception section 2, and the image processing section 9 and the DSC 10 of the image generation section 3.

A movement detection sensor 14 is attached to the ultrasound probe 1, and a movement amount calculation section 15 is connected to the movement detection sensor 14. Further, the portion discrimination section 12 is also connected to the movement amount calculation section 15.

An apparatus controller 16 is connected to the display controller 4, the image analysis section 11, the portion discrimination section 12, the imaging condition setting section 13, and the movement amount calculation section 15. Further, an operation section 17, a storage section 18, and a movement amount reference value memory 19 are respectively connected to the apparatus controller 16.

The array transducer 1A of the ultrasound probe 1 includes a plurality of ultrasound transducers that are arranged in one dimension or two dimensions. Each of the ultrasound transducers transmits ultrasound in accordance with a drive signal supplied from the transmission section 7, and receives an ultrasound echo from a subject to output a reception signal. Each ultrasound transducer is formed using a vibrator in which electrodes are formed on opposite ends of a piezoelectric body formed of piezoelectric ceramics represented as lead zirconate titanate (PZT), a high polymer piezoelectric element represented as polyvinylidene fluoride (PVDF), piezoelectric crystals represented as magnesium niobate-lead titanate solute (PMN-PT), or the like.

In a case where a pulse-shaped voltage or a continuous wave voltage is applied to the electrodes of the vibrator, the piezoelectric body expands and contracts, a pulse-shaped ultrasound or a continuous wave ultrasound is generated from each vibrator, and an ultrasound beam is formed by synthesis of the ultrasounds. Further, each vibrator receives a propagating ultrasound to stretch and compresses to generate an electric signal, and the electric signal is output as an ultrasound reception signal.

The transmission/reception section 2 performs transmission and reception of an ultrasound beam in accordance with a set ultrasound beam scanning condition, and the image generation section 3 generates an ultrasound image signal in accordance with the set ultrasound image generation condition. The transmission/reception section 2 and the image generation section 3 form an imaging section.

Figure 2:
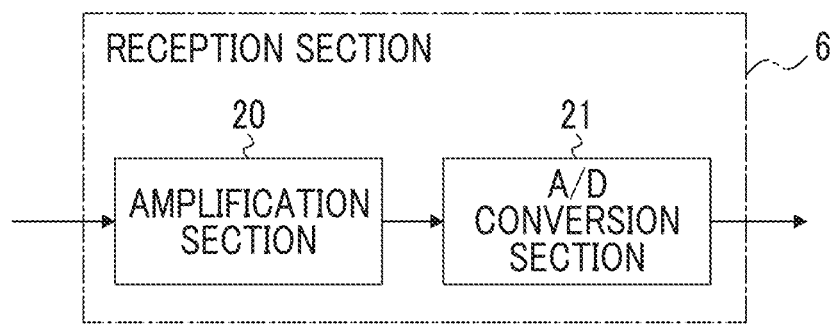
FIG. 2 is a diagram showing a configuration of a reception section.

The reception section 6 of the transmission/reception section 2 has a configuration in which an amplification section 20 and an analogue/digital (A/D) conversion section 21 are sequentially connected in series, as shown in FIG. 2. The reception section 6 amplifies a reception signal transmitted from each ultrasound transducer of the array transducer 1A using the amplification section 20, and performs A/D conversion with respect to the amplified signal using the A/D conversion section 21 to generate digital reception data.

The transmission/reception controller 8 controls the reception section 6 and the transmission section 7 so that transmission of ultrasound pulses to a subject and reception of ultrasound echoes from the subject are repeated at a pulse repetition frequency (PRF) interval, on the basis of various control signals transmitted from the apparatus controller 16.

Figure 3:
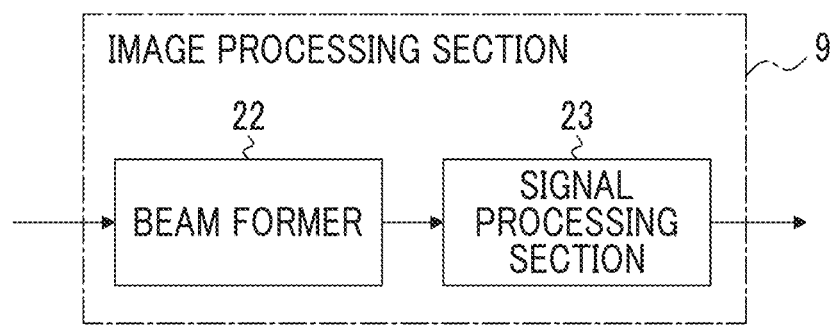
FIG. 3 is a diagram showing a configuration of an image processing section.

The image processing section 9 of the image generation section 3 has a configuration in which a beam former 22 and a signal processing section 23 are sequentially connected in series, as shown in FIG. 3. The beam former 22 assigns a delay to each piece of reception data output from the reception section 6 of the transmission/reception section 2 in accordance with sound velocities set on the basis of a reception delay pattern selected in accordance with control signals from the imaging condition setting section 13 or a distribution of the sound velocities and adds up the results to perform a reception focus process. Through the reception focus process, a sound ray signal in which focuses of ultrasound echoes after phasing addition are narrowed down is generated.

The signal processing section 23 corrects attenuation due to a distance in accordance with a depth of a reflecting position of ultrasound with respect to a sound ray signal generated by the beam former 22, and then, performs an envelope detection process and performs a variety of necessary image processing such as a gradation process, to thereby generate an ultrasound image signal that is tomographic image information of a tissue in a subject.

As the ultrasound image, for example, a brightness mode (B mode) image, a motion mode (M mode) image, a color Doppler imaging, or the like may be used. Further, a sound velocity map indicating a distribution of sound velocities, or an elasticity map indicating a distribution of elasticities indicating smoothness or the like of a tissue in a subject may be used as the ultrasound image.

The DSC 10 of the image generation section 3 converts an ultrasound image signal generated by the signal processing section 23 of the image processing section 9 into an image signal based on a scanning method of a general television signal (raster conversion).

The display section 5 includes a display device such as a liquid crystal display (LCD), for example, and displays an ultrasound image under the control of the display controller 4.

The image analysis section 11 performs image analysis using an ultrasound image from the DSC 10. For example, a feature amount such as a brightness or an edge of the ultrasound image is calculated. Further, in a case where a B mode image signal or an M mode image signal is used, the image analysis may be performed on the basis of a known pattern recognition method such as machine learning, template matching, or texture analysis. In addition, in a case where a color Doppler image signal, a sound velocity map or an elasticity map is used, the image analysis may be performed on the basis of a known method such as color information analysis.

The movement detection sensor 14 is attached to the ultrasound probe 1, and detects a movement of the ultrasound probe 1 in a case where the ultrasound probe 1 is operated by an operator and outputs the movement of the ultrasound probe 1 to the movement amount calculation section 15 as a detection signal. The movement detection sensor 14 is not particularly limited as long as it is possible to detect the movement or position of the ultrasound probe 1, and for example, may be formed by an acceleration sensor, a gyro sensor, a magnetic sensor, a GPS sensor, or other sensors capable of detecting a movement. Further, in order to more accurately detect the movement of the ultrasound probe 1, plural sensors among the above-mentioned sensors may be used in combination.

Figure 4:
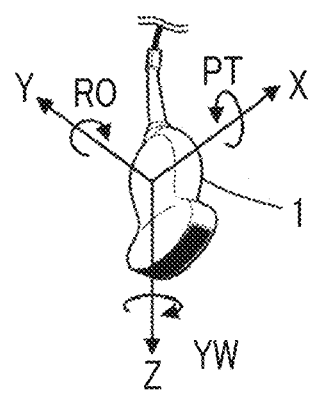
FIG. 4 is a diagram showing an ultrasound probe.

The movement amount calculation section 15 calculates movement amounts of the ultrasound probe 1 in a case where an imaging inspection portion that is currently being imaged is inspected using a detection signal from the movement detection sensor 14 for each frame, and outputs the result to the portion discrimination section 12. Specifically, the movement amount calculation section 15 calculates movement amounts of the ultrasound probe 1 shown in FIG. 4 in each direction. Here, for ease of description, an axis that extends along a direction in which ultrasound is output from the ultrasound probe 1 shown in FIG. 4 is referred to as a Z axis, an axis that crosses the Z axis is referred to as an X axis, and an axis that crosses the Z axis and the X axis is referred to as a Y axis. Further, a rotation direction (pitch) centering around the X axis is referred to as a pitch direction PT, a rotation direction (roll) centering around the Y axis is referred to as a roll direction RO, and a rotation direction (yaw) centering around the Z axis is referred to as a yaw direction YW. That is, the movement amount calculation section 15 calculates a movement amount in a direction along the X axis, a movement amount in a direction along the Y axis, a movement amount in a direction along the Z axis, a movement amount in the roll direction RO, a movement amount in the pitch direction PT, and a movement amount in the yaw direction YW, with respect to the ultrasound probe 1 in a case where the imaging inspection portion that is currently being imaged is inspected.

The movement amount reference value memory 19 stores a plurality of movement amount reference values relating to movement amounts for each inspection portion of the ultrasound probe 1 in advance, in which the plurality of movement amount reference values correspond to a plurality of inspection portions of a subject. For example, generally, in inspection of the lungs, the ultrasound probe 1 is not nearly moved, and in inspection of the abdomen, the ultrasound probe 1 is greatly moved to observe a wide range. In this way, since the movement of the ultrasound probe 1 is changed for each inspection portion, movement amounts of the ultrasound probe 1 in inspection of each inspection portion may be predicted to be set as the movement amount reference values. Further, by comparing the reference values with the movement amounts of the ultrasound probe 1, it is possible to determine which inspection portion is in inspection corresponding to the movement amounts.

As inspection portions of the subject, for example, in the case of extended focused assessment with sonography for trauma (eFAST) inspection, the lungs, the heart, the abdomen, the bladder, and the like may be considered. Portions other than the plurality of inspection portions may be added. Here, among the plurality of inspection portions of the subject, an inspection portion that is currently being imaged is determined as an imaging inspection portion.

The portion discrimination section 12 discriminates an imaging inspection portion that is currently being imaged on the basis of an image analysis result in the image analysis section 11 and movement amounts of the ultrasound probe 1 calculated by the movement amount calculation section 15, and outputs the portion discrimination result to the apparatus controller 16.

Specifically, the portion discrimination section 12 reads out a plurality of movement amount reference values from the movement amount reference value memory 19, and compares each of the plurality of read-out movement amount reference values with each movement amount of the ultrasound probe 1 calculated by the movement amount calculation section 15. Further, the portion discrimination section 12 combines the comparison result and the image analysis result in the image analysis section 11 to discriminate the imaging inspection portion that is currently being imaged. In order to perform the portion discrimination, for example, a support vector machine (SVM) algorithm, a decision tree algorithm, or other known discrimination algorithms may be used.

In this way, the portion discrimination section 12 may integrate the image analysis result and the movement amount of the ultrasound probe 1 to perform the portion discrimination.

The apparatus controller 16 outputs the portion discrimination result output from the portion discrimination section 12 to the imaging condition setting section 13.

Further, the apparatus controller 16 controls the display controller 4, the image analysis section 11, the portion discrimination section 12, the imaging condition setting section 13, and the movement amount calculation section 15 on the basis of commands input through the operation section 17 from the operator.

The imaging condition setting section 13 sets imaging conditions suitable for a discriminated imaging inspection portion with respect to the imaging section formed by the transmission/reception section 2 and the image generation section 3, on the basis of the portion discrimination result input from the apparatus controller 16. The imaging conditions include an ultrasound beam scanning condition for the transmission/reception section 2 and an ultrasound image generation condition for the image generation section 3.

Among the imaging conditions, as the ultrasound beam scanning condition for the transmission/reception section 2, a transmission frequency of an ultrasound beam, a focal position, a display depth, or the like may be used, and as the ultrasound image generation condition for the image generation section 3, a sound velocity, a wave detection condition, a gain, a dynamic range, a gradation curve, a speckle suppression strength, an edge emphasis degree, or the like may be used.

The operation section 17 is a unit through which an operator performs an input operation, and may be formed by a keyboard, a mouse, a trackball, a touch panel, or the like.

The storage section 18 stores an operation program or the like, and may be configured using a recording medium such as a hard disk, a flexible disc, a magneto-optical disc (MO), a magnetic tape (MT), a random access memory (RAM), a compact disc read only memory (CD-ROM), a digital versatile disc read only memory (DVD-ROM), a secure digital card (SD card), a compact flash card (CF card), a universal serial bus memory (USB memory), or a server.

The transmission/reception controller 8 of the transmission/reception section 2, the image generation section 3, the display controller 4, the image analysis section 11, the portion discrimination section 12, the imaging condition setting section 13, the movement amount calculation section 15, and the apparatus controller 16 are configured by a processor including a central processing unit (CPU) and an operation program for causing the CPU to execute various processes, and may be configured by a digital circuit. Further, a configuration in which the transmission/reception controller 8 of the transmission/reception section 2, the image generation section 3, the display controller 4, the image analysis section 11, the portion discrimination section 12, the imaging condition setting section 13, the movement amount calculation section 15, and the apparatus controller 16 are partially or generally integrated into one CPU may be employed.

Next, an operation of Embodiment 1 will be described with reference to a flowchart of FIG. 5.

First, in step S1, transmission and reception and scanning of an ultrasound beam using the plurality of ultrasound transducers of the array transducer 1A of the ultrasound probe 1 are performed by the transmission/reception section 2, a reception signal is output to the reception section 6 from each ultrasound transducer that receives an ultrasound echo from a subject, and is amplified and A/D converted in the reception section 6 to generate reception data.

Then, in step S2, the reception data is input to the image generation section 3, and is subjected to a reception focus process in the image processing section 9. Then, the data is subjected to image conversion in the DSC 10 to generate an ultrasound image signal. The ultrasound image signal is output to the display controller 4 from the image generation section 3, so that an ultrasound image is displayed on the display section 5. Further, the ultrasound image signal is also output to the image analysis section 11.

In step S3, it is determined whether an imaging inspection portion of the ultrasound image signal is changed, by the image analysis section 11. For example, in a case where the imaging inspection portion that is currently being imaged is changed to the heart from the lungs, it is determined that the imaging inspection portion is changed. Specifically, generally, since in a case where the imaging inspection portion is changed, the ultrasound probe 1 is separated from the front surface of the body and performs radiation in the air, by detecting such a radiation state in the air (a state where a reflection signal is not obtained), it is possible to determine the change of the imaging inspection portion. Alternatively, in step S3, in a case where it is determined that the radiation state in the air first shifts to a contact state with respect to a subject, in order to generate an ultrasound image in the imaging inspection portion, the procedure proceeds to step S4.

Through step S4 and S5, the ultrasound image is generated. In step S6, a movement of the ultrasound probe 1 is detected in a case where the imaging inspection portion is inspected by the operator using the movement detection sensor 14 attached to the ultrasound probe 1, and the result is output to the movement amount calculation section 15 as a detection signal. For example, in a case where an acceleration sensor is attached to the ultrasound probe 1 as the movement detection sensor 14, an acceleration is output to the movement amount calculation section 15 as the detection signal.

Further, in step S7, it is determined whether the number of frames F of ultrasound images generated through steps S4 and S5 is equal to or greater than a predetermined number of frames Fs. Until the number of frames F is equal to or greater than the predetermined number of frames Fs, steps S4 to S7 are repeated, and thus, ultrasound images are generated, and movements of the ultrasound probe 1 are detected.

In step S7, in a case where it is determined that the number of frames F is equal to or greater than the predetermined number of frames Fs, a movement amount of the ultrasound probe 1 is calculated by the movement amount calculation section 15, in step S8. The movement amount calculation section 15 calculates a pitch angle that is a rotation angle in the pitch direction PT for each frame, using the detection signal of the acceleration output from the movement detection sensor 14. Thus, for example, a calculation result shown in Table 1 is obtained.

TABLE 1

| Frame Number | N-4 | N-3 | N-2 | N-1 | N |
|---|---|---|---|---|---|
| Pitch angle (degree) | 33 | 33 | 31 | 36 | 38 |
| Pitch angle change (degree) |  | 0 | -2 | 5 | 2 |

In Table 1, the latest frame number is N, and the oldest frame number is N-4. A pitch angle of the frame number N-4 is 33°, and a pitch angle of the next frame number N-3 is 33°. Thus, a change of the pitch angles from the frame number N-4 to N-3 is 0°. A total value of absolute values of the changes of the pitch angles from the frame number N-4 to N, that is, 0+2+5+2=9° may be set as a movement amount of the ultrasound probe 1. The movement amount of the ultrasound probe 1 is not limited to the total value of the absolute values of the changes of the pitch angles between the frames, and may be a total value of absolute values of changes of pitch angles in a predetermined period of time.

As shown in Table 2, by assigning a weight to each frame so that a weight of the most recent frame is the largest, the degree of importance of the most recent frame may be enhanced.

TABLE 2

| Frame Number | N-4 | N-3 | N-2 | N-1 | N |
|---|---|---|---|---|---|
| Pitch angle (degree) | 33 | 33 | 31 | 36 | 38 |
| Pitch angle change (rate) |  | 0 | -2 | 5 | 2 |
| Weight |  | 1 | 2 | 3 | 4 |

A total value of absolute values of changes of pitch angles from the frame number N-4 to N in Table 2 becomes (0×1)+(2×2)+(3×5)+(2×4)=27°, which may be set as a movement amount of the ultrasound probe 1.

In a case where the total value of the absolute values of the changes of the pitch angles from the frame number N-4 to N is calculated, in a case where the ultrasound probe 1 is moved in small steps, it is highly likely that a relatively large value is calculated. On the other hand, in a case where a difference between a maximum value of a minimum value of the pitch angles from the frame number N-4 to N is calculated, even in a case where the ultrasound probe 1 is moved in small steps, it is highly likely that a relatively small value is calculated. In Tables 1 and 2, the difference between the maximum value and the minimum value of the pitch angles from the frame number N-4 to N is 38-31=7°, which may be set as a movement amount of the ultrasound probe 1.

The movement amount of the ultrasound probe 1 calculated by the movement amount calculation section 15 in this way is output to the portion discrimination section 12.

Figure 6:
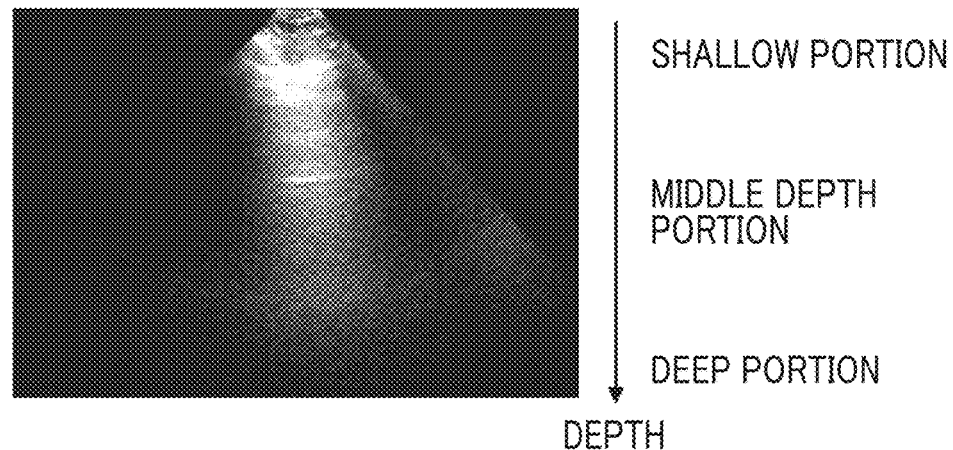
FIG. 6 is a diagram showing an example of an ultrasound image of the lungs.

Further, in step S9, image analysis is performed by the image analysis section 11 using the ultrasound image. The image analysis section 11 calculates a feature amount such as a brightness or an edge of the ultrasound image output from the image generation section 3. For example, it is assumed that an ultrasound image signal for displaying the ultrasound image as shown in FIG. 6 is output to the image analysis section 11 from the image generation section 3. The ultrasound image in FIG. 6 is an example of an ultrasound image of the lungs.

Since the lungs are filled with air and a structure thereof is not easily visualized, in a middle depth portion shown in FIG. 6, the brightness is generally low compared with other inspection portions. Thus, in the middle depth portion, an average value of brightnesses is set as a feature amount. Here, an average value of entire brightnesses in the middle depth portion may be calculated, or a region-of-interest (ROI) may be dividedly set in a depth direction or a lateral direction and an average value of brightnesses in the ROI may be calculated.

Further, since the structure of the lungs is not easily visualized in the middle depth portion, generally, edges are small compared with other portions. Accordingly, after the edges are extracted, an edge area and an edge strength of the middle depth portion are calculated to be set as feature amounts. In this case, the region-of-interest as described above may be dividedly set in the middle depth portion to calculate the edge area and the edge strength.

In the ultrasound image of the lungs, since the pleura are visualized, edges in a lateral direction are present in a shallow portion. Thus, after the edges are extracted, the edge area and the edge strength in the lateral direction in the shallow portion may be calculated as feature amounts.

The image analysis section 11 outputs the feature amounts of the ultrasound image calculated in this way to the portion discrimination section 12 as the image analysis result.

Figure 7:
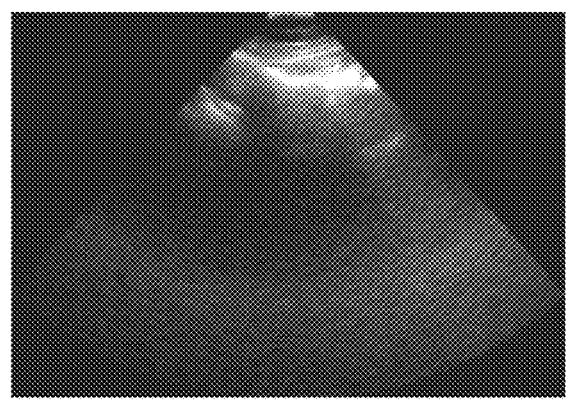
FIG. 7 is a diagram showing an example of an ultrasound image of the abdomen.

In the next step S10, an imaging inspection portion that is currently being imaged is discriminated by the portion discrimination section 12. First, the portion discrimination section 12 distinguishes the lungs from inspection portions other than the lungs on the basis of the image analysis result output from the image analysis section 11. Here, during the inspection of the abdomen, since a structure similar to the lungs may be visualized according to a scanning section, there is a case where it is difficult to distinguish the lungs from the abdomen. For example, an example of an ultrasound image of the abdomen shown in FIG. 7 is similar to the example of the ultrasound image of the lung shown in FIG. 6.

Next, the portion discrimination section 12 reads out movement amount reference values corresponding to inspections of the lungs, the heart, the abdomen, and the bladder from the movement amount reference value memory 19, respectively, and compares each of the movement amount reference values with the movement amount of the ultrasound probe 1 calculated by the movement amount calculation section 15. As described above, generally, in a case where the lungs are inspected, the ultrasound probe 1 is not nearly moved, and in a case where the abdomen is inspected, the ultrasound probe 1 is greatly moved. Accordingly, it is possible to determine whether the inspection of the lungs is performed or the inspection of the abdomen is performed according to the movement amount of the ultrasound probe 1. Further, the movement amount of the ultrasound probe 1 shown in Table 1 is 9°, which represents a very small movement of the ultrasound probe 1. Thus, the portion discrimination section 12 discriminates that the imaging inspection portion is the lungs, and outputs the discrimination result to the apparatus controller 16.

In this way, by integrating the image analysis result in the image analysis section 11 with the movement amount of the ultrasound probe 1 calculated by the movement amount calculation section 15, even in a case where it is difficult to discriminate an imaging inspection portion only using the image analysis result, it is possible to accurately discriminate the imaging inspection portion.

Further, in step S11, the result of the portion discrimination in the portion discrimination section 12 is output to the imaging condition setting section 13 through the apparatus controller 16. The imaging condition setting section 13 sets imaging conditions based on the result of the portion discrimination, and controls the transmission/reception section 2 and the image generation section 3 on the basis of the imaging conditions.

Then, the procedure returns to step S1, and in steps S1 and S2, an ultrasound image is generated in a state where imaging conditions are set by the imaging condition setting section 13, and the ultrasound image is displayed on the display section 5. Until it is determined that the imaging inspection portion is changed by the portion discrimination section 12 in step S3, steps S1 and S2 are repeated, and diagnosis of the lungs that correspond to the imaging inspection portion is continued.

In step S3, in a case where it is determined that the imaging inspection portion is changed, the procedure proceeds to step S4, and imaging conditions for the changed imaging inspection portion are set through steps S4 to S11, and then, steps S1 and S2 are repeated, so that diagnosis of the changed imaging inspection portion may be continued.

In this way, by discriminating an imaging inspection portion that is currently being imaged by integrating an image analysis result with a movement amount of the ultrasound probe, it is possible to accurately discriminate the imaging inspection portion, and to generate an ultrasound image with stable quality to diagnose the imaging inspection portion.

The movement amount calculation section 15 may calculate a movement amount (movement distance) in the direction along the X axis, a movement amount (movement distance) in the direction along the Y axis, a movement amount (movement distance) in the direction along the Z axis, and a movement amount (movement angle) in the roll direction RO and a movement amount (movement angle) in the yaw direction YW, in addition to the movement amount of the ultrasound probe 1 in the pitch direction PT as shown in Table 1. Further, in a state where the movement amounts are calculated, the movement amount calculation section 15 may add up the movement amount in the roll direction RO, the movement amount in the pitch direction PT, and the movement amount in the roll direction RO, and may use the result as an index indicating how much the ultrasound probe 1 swings. Further, the movement amount calculation section 15 may add up the movement amount in the direction along the X axis, the movement amount in the direction along the Y axis, and the movement amount in the direction along the Z axis, and may use the result as an index indicating how much the ultrasound probe 1 slides.

Further, in accordance with a characteristic and a feature of diagnosis for each inspection portion, the portion discrimination section 12 may change movement amounts to be used for execution of the portion discrimination among the movement amounts of the ultrasound probe 1 in the respective directions calculated by the movement amount calculation section 15, for each inspection portion. For example, as described above, generally, in a case where the lungs are inspected, the ultrasound probe 1 is not nearly moved. Thus, since it is considered that the movement amount in the direction along the X axis, the movement amount in the direction along the Y axis, the movement amount in the direction along the Z axis, the movement amount in the roll direction RO, the movement amount in the pitch direction PT, and the movement amount in the yaw direction YW are relatively small, the entirety of these movement amounts may be used. On the other hand, in a case where the heart is inspected, generally, it is considered that variation easily occurs in the change of the movement amount in each direction for each operator due to a habit of an operator in operating the ultrasound probe 1 and easy visualization of an ultrasound image. Thus, the movement amount in the direction along the X axis, the movement amount in the direction along the Y axis, and the movement amount in the direction along the Z axis may be used.

Further, it is also possible to discriminate an imaging inspection portion using the movement amount of the ultrasound probe 1 calculated by the movement amount calculation section 15, in addition to the feature amount calculated through the image analysis, as the feature amount. The movement amount of the ultrasound probe 1 calculated by the movement amount calculation section 15 may be used as the feature amount as it is. Alternatively, an average or a variance of the movement amounts of the ultrasound probe 1 for each inspection portion may be calculated, and the movement amounts may be normalized on the basis of the calculated value to be used as feature amounts.

Figure 8:
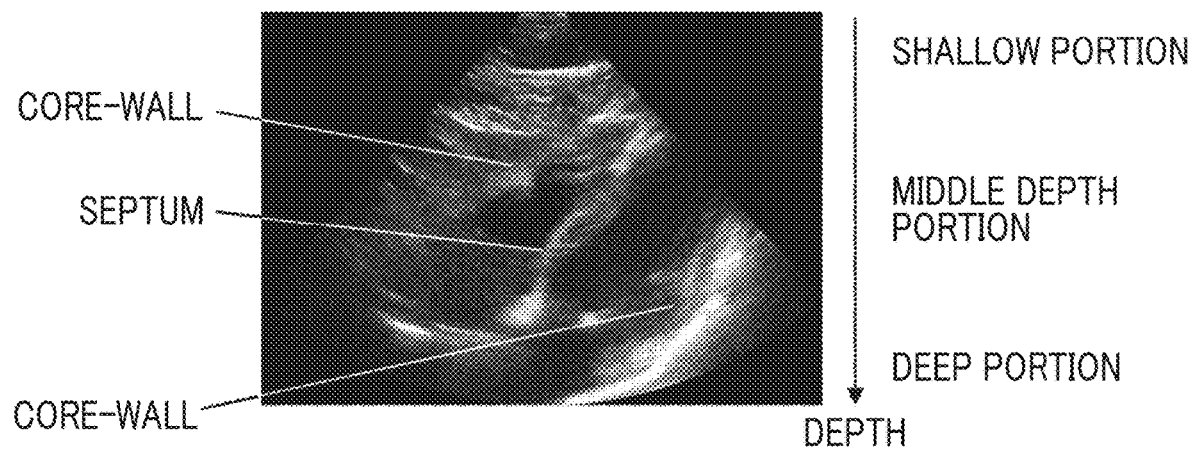
FIG. 8 is a diagram showing an example of an ultrasound image of the heart.

Then, for example, it is assumed that the ultrasound image as shown in FIG. 8 is output to the image analysis section 11. The ultrasound image shown in FIG. 8 is an example of an ultrasound image of the heart.

As shown in FIG. 8, the heart has a variety of edges in an inclined direction due to a core-wall, a septum, and the like in a middle depth portion. Accordingly, after the edges are extracted, it is possible to calculate an edge area and an edge strength of the middle depth portion in the inclined direction. Since the edges are noticeably shown on a right side of the ultrasound image shown in FIG. 8, an edge area and an edge strength may be calculated only on the right side in the middle depth portion.

Further, in the ultrasound image shown in FIG. 8, since the core-wall and the septum are displayed as white edges and blood is present between the core-wall and the septum, a space between the core-wall and the septum is displayed as a dark region. Thus, the white edges and the black region are displayed in parallel as a pattern. Accordingly, by calculating a score through pattern recognition with respect to the pattern or digitizing the degree of brightness change using a profile of the brightness change or the like, it is possible to calculate feature amounts.

Figure 9:
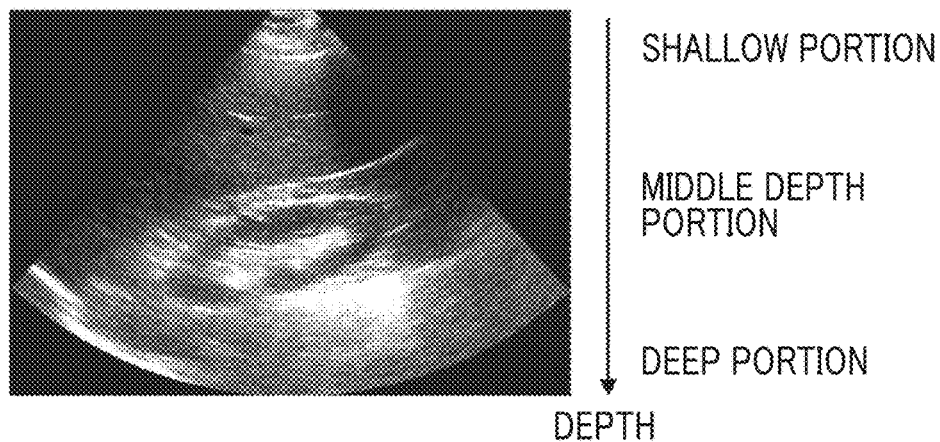
FIG. 9 is a diagram showing an example of an ultrasound image of the right abdomen.

On the basis of the feature amounts calculated in this way, the heart and inspection portions other than the heart are distinguished from each other. Here, since the structure similar to the heart may be visualized according to a scanning section during inspection of the abdomen, there is a case where it is difficult to distinguish the heart from the right abdomen. For example, in a case where an example of an ultrasound image of the right abdomen shown in FIG. 9 is compared with the example of the ultrasound image of the heart shown in FIG. 8, there are many edges in an inclined direction in the middle depth portions in both the cases, which shows that both the cases are similar to each other.

On the other hand, focusing on the movement of the ultrasound probe 1, generally, in a case where the heart is inspected, the ultrasound probe 1 is not greatly moved in the direction along the X axis, the direction along the Y axis, and the direction along the Z axis, that is, in a sliding direction. On the other hand, as described above, in a case where the abdomen is inspected, the ultrasound probe 1 is greatly moved.

Figure 10:
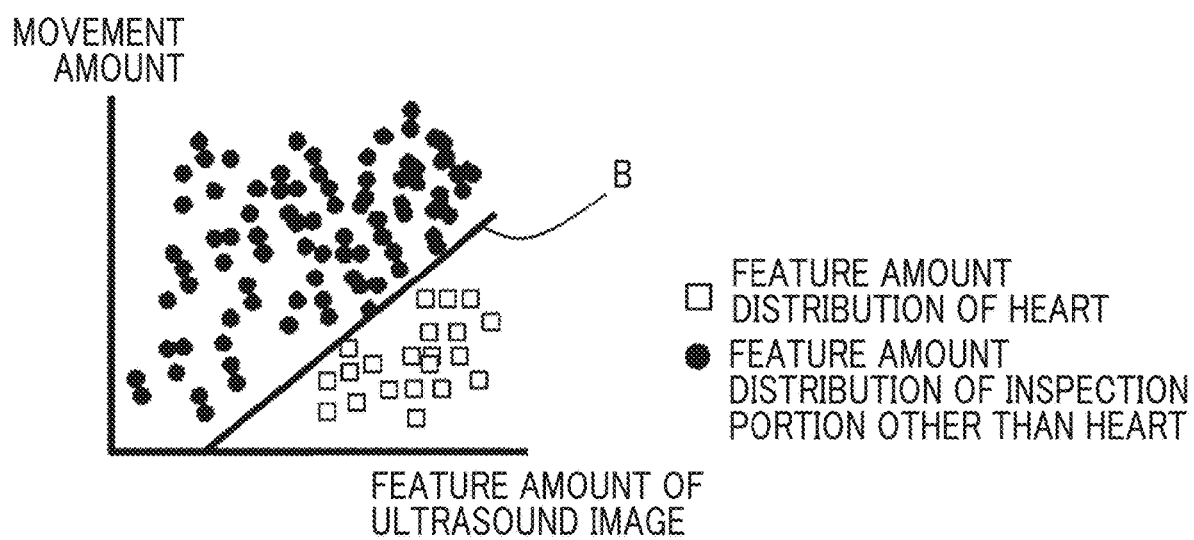
FIG. 10 is a diagram showing an example of distribution of feature amounts.

Accordingly, for example, as shown in FIG. 10, it is possible to calculate a distribution of feature amounts of the heart and a distribution of inspection portions other than the heart by causing a longitudinal axis to represent a movement amount (feature amount) of the ultrasound probe 1 and a lateral axis to represent a feature amount of an ultrasound image, and to distinguish the heart and the abdomen with reference to a boundary B between the heart and the inspection portions other than the heart. In FIG. 10, an edge strength and an edge area in an inclined direction in a middle depth portion are used as feature amounts of an ultrasound image, for example. Further, a sum of a movement amount in the direction along the X axis, a movement amount in the direction along the Y direction, and a movement amount in the direction along the Z axis may be used as the movement amount of the ultrasound probe 1, for example.

In addition, in comparing the inspection of the heart with the inspection of the lung, as described above, in a case where the heart is inspected, the ultrasound probe 1 is not greatly moved in the direction along the X axis, the direction along the Y axis, and the direction along the Z axis, and in a case where the lungs are inspected, the ultrasound probe 1 is not greatly moved in any direction. That is, it is difficult to distinguish the heart from the lungs only using the movement amount of the ultrasound probe 1. On the other hand, as shown in FIG. 6, since edges are not nearly present in the inclined direction in the example of the ultrasound image of the lungs, feature amounts of the ultrasound images of the lungs and the heart are different from each other. Accordingly, in the distributions of the feature amounts of the heart and the inspection portions other than the heart shown in FIG. 10, it is possible to distinguish the heart from the lungs with reference to the boundary B between the heart and the inspection portions other than the heart.

In FIG. 10, the edge strength and the edge area in the inclined direction in the middle depth portion are used as the feature amounts of the ultrasound image, but a brightness may be added thereto. Further, the sum of the movement amount in the direction along the X axis, the movement amount in the direction along the Y direction, and the movement amount in the direction along the Z axis are used as the movement amount of the ultrasound probe 1, but a movement amount in the pitch direction PT, a movement amount in the roll direction RO, and a movement amount in the yaw direction YW may be added thereto. Thus, it is possible to calculate a distribution of feature amounts in multi dimensions.

Embodiment 2

In Embodiment 1, the portion discrimination section 12 integrates an image analysis result and a movement amount of the ultrasound probe 1 to perform portion discrimination. On the other hand, in Embodiment 2, the portion discrimination section 12 narrows down a plurality of inspection portions that are targets of image analysis, on the basis of a movement amount of the ultrasound probe 1.

Figure 5:
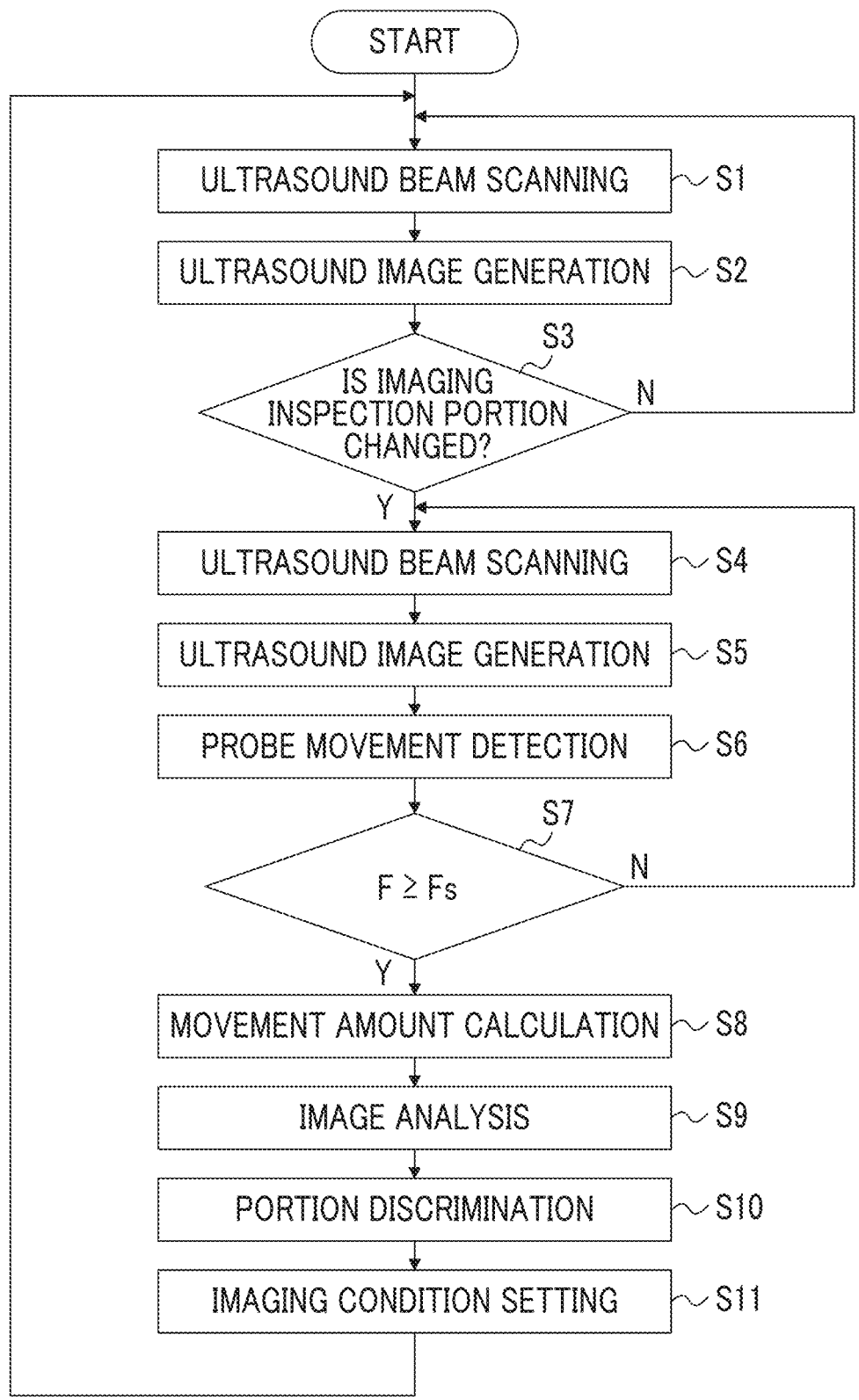
FIG. 5 is a flowchart showing an operation of Embodiment 1.

An ultrasound image is generated through steps S1 to S7 in the flowchart of FIG. 5, and a movement of the ultrasound probe 1 is detected. Then, movement amounts of the ultrasound probe 1 as shown in the following Table 3 are calculated by the movement amount calculation section 15 in step S8, for example.

TABLE 3

|  | Pitch direction PT | Roll direction RO | Yaw direction YW | Direction along X axis | Direction along Y axis | Direction along Z axis |
| --- | --- | --- | --- | --- | --- | --- |
| Movement amount | 3 | 4 | 3 | 1 | 0 | 6 |
| Setting range | 0 to 5 | 0 to 5 | 0 to 5 | 0 to 5 | 0 to 5 | 0 to 5 |

The movement amounts shown in Table 3 are obtained by adding up absolute values of changes of movement amounts between predetermined frames as described above and normalizing the total values. Calculation results of the movement amounts are output to the portion discrimination section 12.

In the next step S9, in performing image analysis using an ultrasound image by the image analysis section 11, inspection portions that are targets of the image analysis are narrowed down by the portion discrimination section 12. The portion discrimination section 12 reads out a plurality of movement amount reference values corresponding to a plurality of inspection portions from the movement amount reference value memory 19, and sets setting ranges with respect to movement amounts in respective directions of the ultrasound probe 1, as shown in Table 3, on the basis of the plurality of movement amount reference values.

As described above, generally, in a case where the lungs are inspected, the ultrasound probe 1 is not nearly moved. Thus, as shown in Table 3, setting ranges of 0 to 5 are provided with respect to the movement amounts in the respective directions. In a case where any movement amount among the movement amounts in the respective directions exceeds an upper limit value of the setting range, it is possible to determine that the image analysis is not performed with respect to the lungs. In Table 3, since the movement amount in the direction along the Z axis is 6 and exceeds the upper limit of the setting range, the image analysis is not performed with respect to the lungs for a predetermined period of time.

Here, the period of time during which the image analysis is not performed with respect to the lungs may be set to any one of a period of time between frames where the movement amounts of the ultrasound probe 1 are calculated, a period of time until a predetermined period of time elapses after an ultrasound image corresponding to a frame where the movement amounts are calculated is generated, or a period of time until inspection of an imaging inspection portion that is currently being imaged is terminated after the ultrasound image corresponding to the frame where the movement amounts are calculated is generated. The period of time when the image analysis is not performed with respect to the lungs may be set in advance from these periods of time, and may be changed in accordance with how much the movement amount of the ultrasound probe 1 and the setting range corresponding to the movement amount are spaced from each other.

Further, as described above, generally, in a case where the heart is inspected, variation in changes of movement amounts in respective directions for each operator easily occurs. Further, it is considered that the ultrasound probe 1 is greatly moved compared with the inspection of the lungs. Accordingly, the portion discrimination section 12 may provide setting ranges of 0 to 10 with respect to the movement amount in the direction along the X axis, the movement amount in the direction along the Y axis, and the movement amount in the direction along the Z axis, as shown in Table 4, on the basis of the plurality of movement amount reference values.

TABLE 4

|  | Pitch direction PT | Roll direction RO | Yaw direction YW | Direction along X axis | Direction along Y axis | Direction along Z axis |
| --- | --- | --- | --- | --- | --- | --- |
| Movement amount | 3 | 4 | 3 | 1 | 0 | 6 |
| Setting range | — | — | — | 0 to 10 | 0 to 10 | 0 to 10 |

In Table 4, since the movement amount in the direction along the Z axis is 6 and is within the setting range, the image analysis is performed with respect to the heart.

Further, generally, in a case where the bladder is inspected, the ultrasound probe 1 is greatly moved in the pitch direction PT or the direction along the Y axis so that the entire bladder is viewed. Accordingly, as shown in Table 5, a setting range of 30 or greater may be set with respect to the movement amount in the pitch direction PT or the movement amount in the direction along the Y axis. Further, in a case where the movement amount in any direction does not reach the lower limit value of the setting range, it is possible to determine that the image analysis is not performed with respect to the bladder.

TABLE 5

|  | Pitch direction PT | Roll direction RO | Yaw direction YW | Direction along X axis | Direction along Y axis | Direction along Z axis |
|---|---|---|---|---|---|---|
| Movement amount | 3 | 4 | 3 | 1 | 0 | 6 |
| Setting range | 30 or greater | — | — | — | 30 or greater | — |

In Table 5, since the movement amount in the pitch direction PT is 3 and the movement amount in the direction along the Y axis is 0, that is, any movement amount does not reach the lower limit value of the setting range, the image analysis is not performed with respect to the bladder for a predetermined period of time.

As described above, a plurality of inspection portions that are targets of image analysis are narrowed down by the portion discrimination section 12 on the basis of the movement amounts of the ultrasound probe 1, and the narrow-down result of the inspection portions is output to the image analysis section 11.

Further, the image analysis section 11 performs image analysis with respect to the plurality of inspection portions that are narrowed down by the portion discrimination section 12, and outputs the image analysis result to the portion discrimination section 12. In the next step S10, the portion discrimination section 12 discriminates an imaging inspection portion using the image analysis result.

In this way, by narrowing down inspection portions that are targets of image analysis on the basis of movement amounts of the ultrasound probe 1, it is possible to reduce the number of image analysis processes for which it is generally considered that a processing load is high, and to effectively reduce the processing load due to the image analysis processes.

The portion discrimination section 12 may integrate the image analysis results for the inspection portions that are narrowed down by the portion discrimination section 12 and the movement amounts of the ultrasound probe 1 calculated by the movement amount calculation section 15 to discriminate the imaging inspection portion that is currently being imaged. By narrowing down the inspection portions, it is possible to accurately discriminate the imaging inspection portion while reducing the processing load due to the image analysis processes.

Further, in narrowing down the inspection portions, in order to prevent inspection portions from being overlooked, setting ranges with respect to movement amounts are provided to be wide to some extent, and thus, there is a possibility that the inspection portions may not be sufficiently narrowed down. However, even though the inspection portions are not sufficiently narrowed down, it is possible to accurately discriminate the imaging inspection portion by integrating the image analysis results with the movement amounts of the ultrasound probe 1.

Embodiment 3

In Embodiment 1 and Embodiment 2, an analysis order for performing image analysis with respect to a plurality of inspection portions is not fixed, but in Embodiment 3, the analysis order is determined on the basis of movement amounts of the ultrasound probe 1.

An ultrasound image is generated through steps S1 to S7 in the flowchart of FIG. 5 and the movements of the ultrasound probe 1 are detected. In step S8, it is assumed that the movement amounts of the ultrasound probe 1 as shown in the following Table 6 are calculated by the movement amount calculation section 15 and are output to the portion discrimination section 12.

TABLE 6

|  | Pitch direction PT | Roll direction RO | Yaw direction YW | Direction along X axis | Direction along Y axis | Direction along Z axis |
|---|---|---|---|---|---|---|
| Movement amount | 3 | 4 | 3 | 1 | 0 | 3 |
| Setting range | 0 to 5 | 0 to 5 | 0 to 5 | 0 to 5 | 0 to 5 | 0 to 5 |

In the next step S9, in performing image analysis by the image analysis section 11, an analysis order for performing the image analysis with respect to a plurality of inspection portions is determined by the portion discrimination section 12. The portion discrimination section 12 reads out a plurality of movement amount reference values corresponding to the plurality of inspection portions from the movement amount reference value memory 19, and sets setting ranges with respect to the movement amounts of the ultrasound probe 1 as shown in Table 6, on the basis of the plurality of movement amount reference values.

As described above, generally, in a case where the lungs are inspected, the ultrasound probe 1 is not nearly moved. Thus, as shown in Table 6, setting ranges of 0 to 5 are set with respect to movement amounts in the respective directions, and in a case where the movement amounts in the respective directions are within the setting ranges, it is possible to determine that the image analysis is preferentially performed with respect to the lungs. In Table 3, since the movement amounts in the respective directions are within the setting ranges, the image analysis is preferentially performed with respect to the lungs. Further, by setting ranges with respect to movement amounts of the ultrasound probe 1 on the basis of movement amount reference values corresponding to inspection portions other than the lungs and comparing the setting ranges with the movement amounts of the ultrasound probe 1, an analysis order for performing image analysis with respect to the plurality of inspection portions is determined, and the determined analysis inspection order is output to the image analysis section 11.

Further, the image analysis section 11 preferentially performs image analysis with respect to the lungs among the plurality of inspection portions, in accordance with the analysis order determined by the portion discrimination section 12, and outputs the image analysis result to the portion discrimination section 12. Further, in step S10, the portion discrimination section 12 discriminates an imaging inspection portion using the image analysis result. Here, since it is determined in advance by the portion discrimination section 12 that there is a high possibility that the imaging inspection portion corresponds to the lungs on the basis of the movement amount of the ultrasound probe 1, a possibility that it is discriminated that the imaging inspection portion corresponds to the lungs becomes high.

In this way, by determining an analysis order for performing image analysis with respect to a plurality of inspection portions, it is possible to discriminate an imaging inspection portion in a short time, and thus, it is possible to enhance response performance of the ultrasound diagnostic apparatus according to Embodiment 3.

Further, as shown in the following Table 7 and Table 8, it is also possible to set setting ranges with respect to movement amounts of the ultrasound probe 1 in two stages of narrowing down of a plurality of inspection portions and an analysis order for performing image analysis with respect to the plurality of inspection portions.

ence values, regardless of an operator or a subject, but in Embodiment 4, movement amount reference values are corrected for each operator or subject, and are compared with the movement amounts of the ultrasound probe 1.

Figure 11:
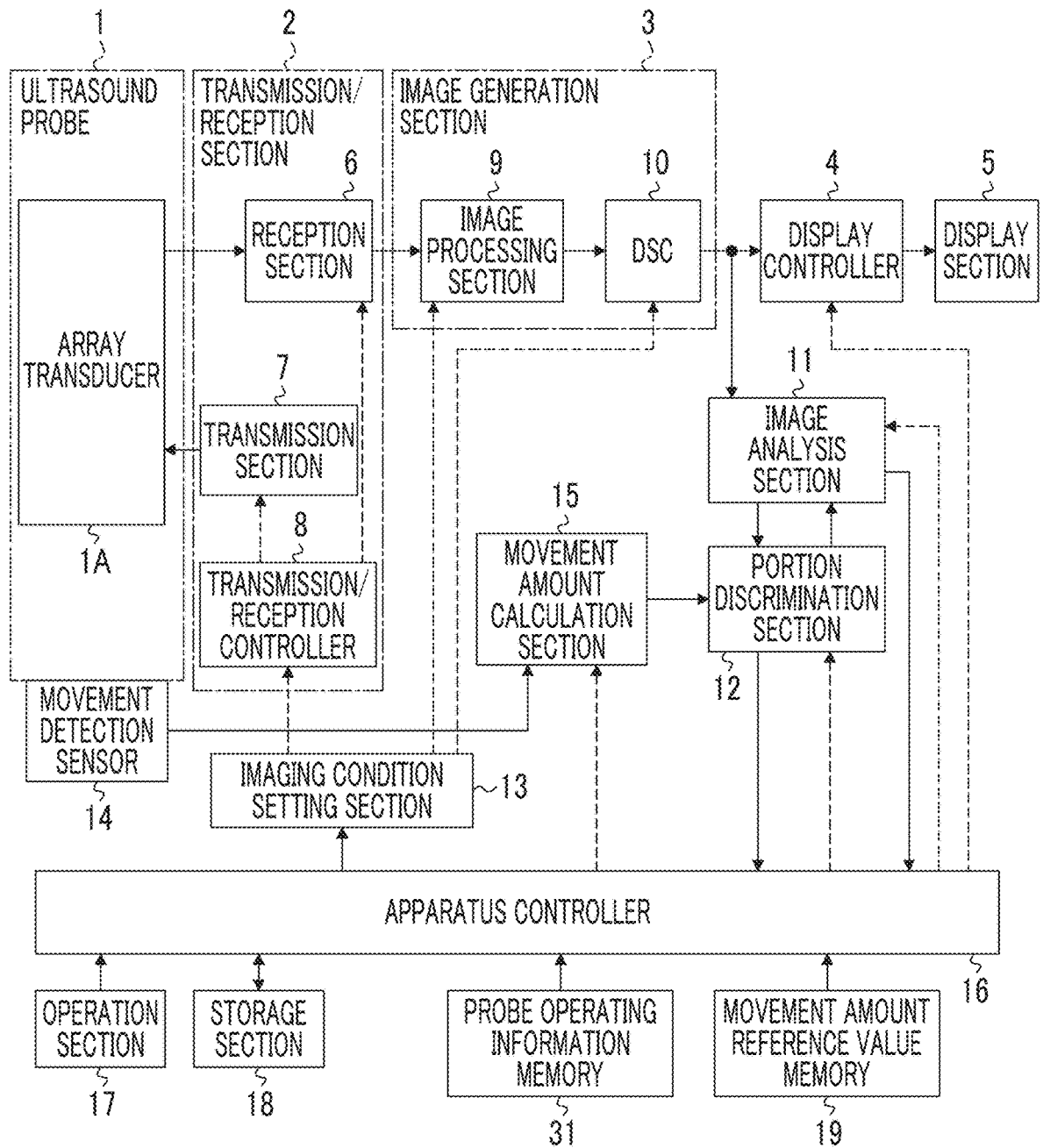
FIG. 11 is a diagram showing a configuration of ultrasound diagnosis apparatus according to Embodiment 4.

FIG. 11 shows a configuration of an ultrasound diagnostic apparatus according to Embodiment 4. The ultrasound diagnostic apparatus according to Embodiment 4 comprises a probe operating information memory 31, in the configuration of the ultrasound diagnostic apparatus according to Embodiment 1 shown in FIG. 1, and the probe operating information memory 31 is connected to the apparatus controller 16.

The probe operating information memory 31 stores in advance information relating to an operation of the ultrasound probe 1 for each operator or subject. In operating the ultrasound probe 1, it is considered that there is a feature or a habit in an operating way of the ultrasound probe 1 for each operator, such as an angle of the ultrasound probe on a subject or a moving way of the ultrasound probe 1, for example. Further, in operating the ultrasound probe 1, in accordance with the type of a subject, for example, in accordance with a child or an adult, it is considered that an operating way of the ultrasound probe 1 is changed. Thus, it

TABLE 7

|  | Pitch direction PT | Roll direction RO | Yaw direction YW | Direction along X axis | Direction along Y axis | Direction along Z axis |
| --- | --- | --- | --- | --- | --- | --- |
| Movement amount | 3 | 4 | 3 | 1 | 0 | 6 |
| Setting range (analysis order) | 0 to 5 | 0 to 5 | 0 to 5 | 0 to 5 | 0 to 5 | 0 to 5 |
| Setting range (narrowing down) | 0 to 10 | 0 to 10 | 0 to 10 | 0 to 10 | 0 to 10 | 0 to 10 |

TABLE 8

|  | Pitch direction PT | Roll direction RO | Yaw direction YW | Direction along X axis | Direction along Y axis | Direction along Z axis |
| --- | --- | --- | --- | --- | --- | --- |
| Movement amount | 3 | 4 | 3 | 1 | 0 | 22 |
| Setting range (analysis order) | 0 to 5 | 0 to 5 | 0 to 5 | 0 to 5 | 0 to 5 | 0 to 5 |
| Setting range (narrowing down) | 0 to 10 | 0 to 10 | 0 to 10 | 0 to 10 | 0 to 10 | 0 to 10 |

For example, in a case where movement amounts of the ultrasound probe 1 as shown in Table 7 are calculated, a movement amount in the direction along the Z axis is 6, and exceeds an upper limit of a setting range relating to an analysis order. Thus, image analysis for an inspection portion corresponding to the movement amount is performed after image analysis for a different inspection portion. Further, for example, in a case where movement amounts of the ultrasound probe 1 as shown in FIG. 8 are calculated, a movement amount in the direction along the Z axis is 22, and exceeds an upper limit of a setting range relating to narrowing down. Thus, image analysis is not performed with respect to an inspection portion corresponding to the movement amount.

Embodiment 4

In Embodiments 1 to 3, movement amounts of the ultrasound probe 1 are compared with movement amount referis possible to collect in advance the information relating to the operation of the ultrasound probe 1 for each operator or subject.

For example, an operator inputs information on the operator or a subject to the ultrasound diagnostic apparatus according to Embodiment 4 through the operation section 17, and the portion discrimination section 12 reads out information relating to an operation of the ultrasound probe 1 from the probe operating information memory 31 on the basis of the input information. Further, the portion discrimination section 12 corrects a plurality of movement amount reference values of the movement amount reference value memory 19 on the basis of the information, and compares the plurality of corrected movement amount reference values with movement amounts of the ultrasound probe 1. Thus, it is possible to discriminate an imaging inspection portion in accordance with an operator or a subject, it is possible to enhance the accuracy of portion discrimination.

In a case where the information relating to the operation of the ultrasound probe 1 corresponding to the input information on the subject is not stored in the probe operating information memory 31, information on a different subject that is common in weight, height, gender, body fat rate, or the like may be used.

EXPLANATION OF REFERENCES

1: ultrasound probe
1A: array transducer
2: transmission/reception section
3: image generation section
4: display controller
5: display section
6: reception section
7: transmission section
8: transmission/reception controller
9: image processing section
10: DSC
11: image analysis section
12: portion discrimination section
13: imaging condition setting section
14: movement detection sensor
15: movement amount calculation section
16: apparatus controller
17: operation section
18: storage section
19: movement amount reference value memory
20: amplification section
21: A/D conversion section
22: beam former
23: signal processing section
31: probe operating information memory
X, Y, Z: axis
PT, RO, YW: direction
B: boundary

What is claimed is:

1. A control method of an ultrasound diagnostic apparatus comprising:
   transmitting an ultrasound beam toward a subject from an ultrasound probe;
   generating reception data on the basis of signals output from the ultrasound probe;
   imaging the subject on the basis of the generated reception data to generate an ultrasound image;
   performing image analysis using the generated ultrasound image;
   detecting a movement of the ultrasound probe to output the movement as a detection signal;
   storing in advance a plurality of movement amount reference values corresponding to a plurality of inspection portions of a plurality of different organs of the subject in a movement amount reference value memory, each of the plurality of movement amount reference values representing a movement amount of the ultrasound probe moved while inspecting the corresponding inspection portion;
   storing in advance information relating to an operation of the ultrasound probe for each inspector or each subject in a probe operating information memory;
   calculating a movement amount of the ultrasound probe while inspecting an imaging inspection portion that is currently being imaged among the plurality of inspection portions of the subject, using the output detection signal;
   reading out the information relating to the operation of the ultrasound probe from the probe operating information memory;
   reading out the plurality of movement amount reference values from the movement amount reference value memory to correct the plurality of movement reference values on the basis of the read-out information so that the information relating to the operation of the ultrasound probe for each inspector or each subject is taken into account;
   comparing each of the plurality of corrected movement amount reference values with the movement amount of the ultrasound probe; and
   discriminating the imaging inspection portion on the basis of the comparison result and the result of the image analysis.

2. An ultrasound diagnostic apparatus comprising:
   an ultrasound probe;
   a transmission circuit that transmits an ultrasound beam toward a subject from the ultrasound probe;
   a reception circuit that generates reception data on the basis of signals output from the ultrasound probe;
   a movement detection sensor that is attached to the ultrasound probe and detects a movement of the ultrasound probe to output the movement as a detection signal;
   a movement amount reference value memory in which a plurality of movement amount reference values corresponding to a plurality of inspection portions of a plurality of different organs of the subject are stored in advance, each of the plurality of movement amount reference values representing a movement amount of the ultrasound probe moved while inspecting the corresponding inspection portion;
   a probe operating information memory in which information relating to an operation of the ultrasound probe is stored in advance for each inspector or each subject, and
   a processor that
     images the subject on the basis of the reception data generated by the reception circuit to generate an ultrasound image,
     performs image analysis using the generated ultrasound image,
     calculates a movement amount of the ultrasound probe while inspecting an imaging inspection portion that is currently being imaged among the plurality of inspection portions of the subject, using the detection signal output from the movement detection sensor,
     reads out the information relating to the operation of the ultrasound probe from the probe operating information memory,
     reads out the plurality of movement amount reference values from the movement amount reference value memory,
     corrects the plurality of movement amount reference values on the basis of the read-out information so that the information relating to the operation of the ultrasound probe for each inspector or each subject is taken into account,
     compares each of the plurality of corrected movement amount reference values with the movement amount of the ultrasound probe, and
     discriminates the imaging inspection portion on the basis of the comparison result and the result of the image analysis.

3. The ultrasound diagnostic apparatus according to claim 2,
wherein the processor integrates the comparison result and the result of the image analysis to discriminate the imaging inspection portion.

4. The ultrasound diagnostic apparatus according to claim 3,
wherein the processor performs the image analysis using the ultrasound image to calculate a feature amount of the ultrasound image, and integrates the feature amount and the comparison result to discriminate the imaging inspection portion.

5. The ultrasound diagnostic apparatus according to claim 2,
wherein the processor narrows down the plurality of inspection portions that are targets of the image analysis, on the basis of the movement amount of the ultrasound probe, performs the image analysis with respect to the narrowed-down inspection portions to acquire the result of the image analysis.

6. The ultrasound diagnostic apparatus according to claim 2,
wherein the processor determines an analysis order for performing the image analysis with respect to the plurality of inspection portions, on the basis of the movement amount of the ultrasound probe, sequentially performs the image analysis with respect to the plurality of inspection portions in accordance with the determined analysis order to acquire the result of the image analysis.

7. The ultrasound diagnostic apparatus according to claim 2,
wherein the processor narrows down the plurality of inspection portions that are targets of the image analysis and determines an analysis order for performing the image analysis with respect to the plurality of inspection portions, on the basis of the movement amount of the ultrasound probe, sequentially performs the image analysis with respect to the narrowed-down inspection portions in accordance with the determined analysis order to acquire the result of the image analysis.

8. The ultrasound diagnostic apparatus according to claim 2
wherein the processor sets an imaging condition corresponding to the discriminated imaging inspection portion, and generates the ultrasound image in accordance with the set imaging condition.

9. The ultrasound diagnostic apparatus according to claim 2,
wherein the movement detection sensor is formed by an acceleration sensor, a gyro sensor, a magnetic sensor, or a GPS sensor.

* * * * *